(12) United States Patent
Stevens

(10) Patent No.: US 6,529,018 B1
(45) Date of Patent: Mar. 4, 2003

(54) METHOD FOR MONITORING DEFECTS IN POLYSILICON GATES IN SEMICONDUCTOR DEVICES RESPONSIVE TO ILLUMINATION BY INCIDENT LIGHT

(75) Inventor: Keith C. Stevens, Fairfield, VT (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 09/141,830

(22) Filed: Aug. 28, 1998

(51) Int. Cl.[7] ............................................... G01R 31/28
(52) U.S. Cl. ........................ 324/750; 324/751; 324/765
(58) Field of Search ................................. 324/750, 765, 324/751, 752; 250/559.07; 356/237.5, 376, 400, 401

(56) References Cited

U.S. PATENT DOCUMENTS

| 4,680,635 A | | 7/1987 | Khurana et al. |
| 4,755,874 A | | 7/1988 | Esrig et al. |
| 4,811,090 A | | 3/1989 | Khurana |
| 4,983,830 A | * | 1/1991 | Iwasaki ....................... 250/309 |
| 5,006,717 A | | 4/1991 | Tsutsu et al. |
| 5,136,373 A | | 8/1992 | Kamiya et al. |
| 5,193,120 A | * | 3/1993 | Gamache et al. ............ 356/376 |
| 5,329,139 A | | 7/1994 | Sanada |
| 5,391,885 A | | 2/1995 | Imataki et al. |
| 5,430,305 A | * | 7/1995 | Cole, Jr. et al. ......... 250/559.07 |
| 5,504,431 A | | 4/1996 | Maeda et al. |
| 5,532,873 A | | 7/1996 | Dixon |
| 5,966,019 A | * | 10/1999 | Borden ........................ 324/752 |
| 6,081,127 A | * | 6/2000 | Wagner et al. ............... 324/752 |

* cited by examiner

Primary Examiner—Vinh P. Nguyen
(74) Attorney, Agent, or Firm—Scully, Scott, Murphy & Presser; Anthony Canale, Esq.

(57) ABSTRACT

A method of detecting defects in a semiconductor device by providing the semiconductor device with an electron-generating photodiode region to be used as a circuit stimulus in response to incident light, and also with conductive paths connecting the photodiode electron-generating region to terminals of polysilicon gate areas. The photodiode region of the semiconductor device is illuminated with light to stimulate the semiconductor device, and light emitted therefrom is detected. The semiconductor device can consist of a silicon chip, particularly a polysilicon gated field effect transistor silicon chip, wherein the photodiode electron-generating region possesses a diffused region therein.

5 Claims, 1 Drawing Sheet

METHOD FOR MONITORING DEFECTS IN POLYSILICON GATES IN SEMICONDUCTOR DEVICES RESPONSIVE TO ILLUMINATION BY INCIDENT LIGHT

BACKGROUND OF THE INVENTION

1. Field of the Invention

The present invention relates generally to a method and structure for monitoring polysilicon gate defects. More particularly, the subject invention pertains to a method and structure for monitoring polysilicon gate defects in a semiconductor device by providing the semiconductor device with an electron-generating photodiode region to be used as a circuit stimulus in response to incident light, and also with conductive paths connecting the photodiode electron-generating region to terminals of the polysilicon gate areas. The photodiode region of the semiconductor device is illuminated with light to stimulate the semiconductor device, and light is detected which is emitted therefrom.

2. Discussion of the Prior Art

Currently, test probing of polysilicon lines on silicon chips is performed with mechanical test probes. The mechanical test probes frequently break off chips of polysilicon, which then often short adjacent polysilicon lines.

SUMMARY OF THE INVENTION

It is a primary object of the present invention to provide a method and structure for monitoring polysilicon gate defects.

A further object of the subject invention is the provision of a method and structure for monitoring polysilicon gate defects which provides:

- early defect monitor testing during the manufacture of integrated circuits;
- a low cost testing method utilized during the manufacture of integrated circuits;
- an elimination of defects caused by physical contact of mechanical test probes during defect monitor testing;
- a reduction in additional manufacturing process steps to account for physical test probing;

In accordance with the teachings herein, the present invention provides a method of detecting defects in a semiconductor device by providing the semiconductor device with an electron-generating photodiode region to be used as a circuit stimulus in response to incident light, illuminating the photodiode region of the semiconductor device with light to stimulate the semiconductor device, and detecting light emitted therefrom.

In greater detail, the semiconductor device is illuminated with light at a first wavelength, and light is detected emitted by the semiconductor device at a second wavelength, different from the first wavelength. The detected light emitted by the illuminated semiconductor device is filtered to remove light at the first wavelength.

The semiconductor device comprises a silicon chip, particularly a polysilicon gated field effect transistor silicon chip, and the photodiode electron-generating region comprises a diffused region in the silicon chip. Moreover, light is detected which is emitted from polysilicon gate areas of the silicon chip. The silicon chip is also provided with conductive paths connecting the photodiode electron-generating region to terminals of the polysilicon gate areas, although some embodiments of the present invention may not require such conductive paths.

The photodiode region is illuminated with a laser beam, and the power of the laser beam can be selectively varied to provide multiple images under different test conditions.

An image is formed of light emitted by the semiconductor device, and the image is captured and analyzed in a computer having a frame acquisition capability.

BRIEF DESCRIPTION OF THE DRAWINGS

The foregoing objects and advantages of the present invention for a method and structure for monitoring polysilicon gate defects may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1A:
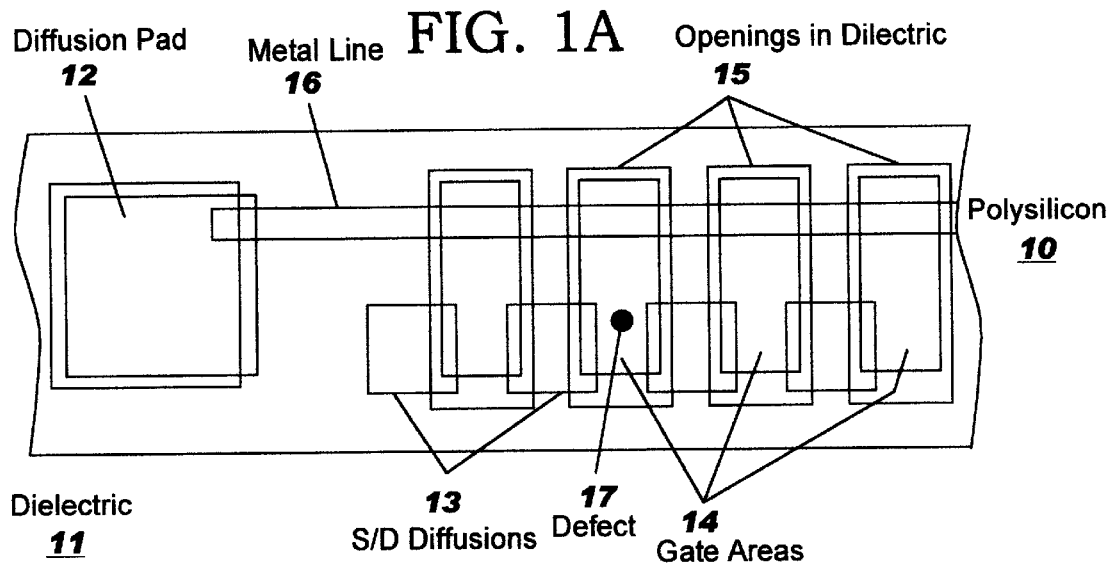
FIGS. 1A and 1B are respectively a top plan view and a side elevational view of an exemplary integrated circuit silicon chip test structure pursuant to the present invention.
Figure 1B:
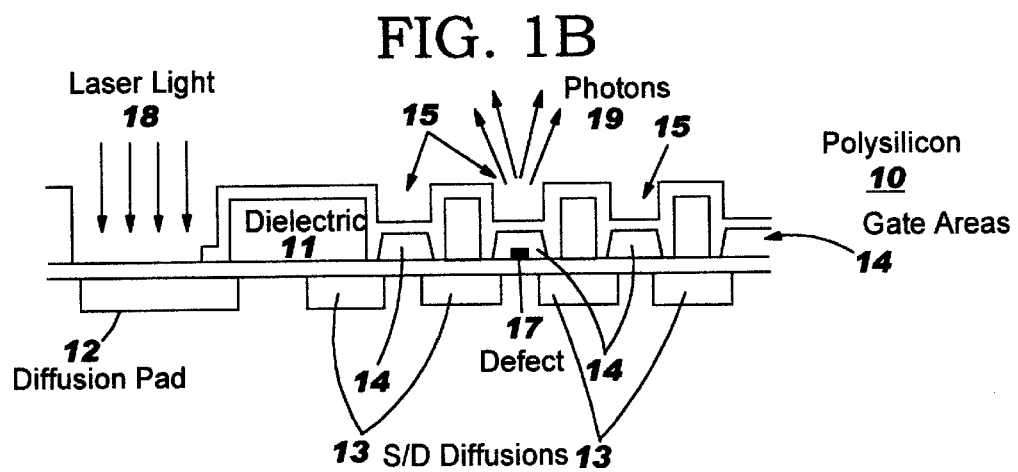

Referring to the drawings in detail, FIGS. 1A and 1B are respectively a top plan view and a side elevational view of an integrated circuit test structure. The test structure comprises a silicon chip formed on a polysilicon substrate 10, having dielectric regions 11, a diffusion pad 12 similar to a Source/Drain (S/D) diffusion region, S/D diffusions 13, gate areas 14, openings 15 in the dielectric, and a metal line 16 extending from the diffusion pad 12 to the gate areas 14.

Figure 2:
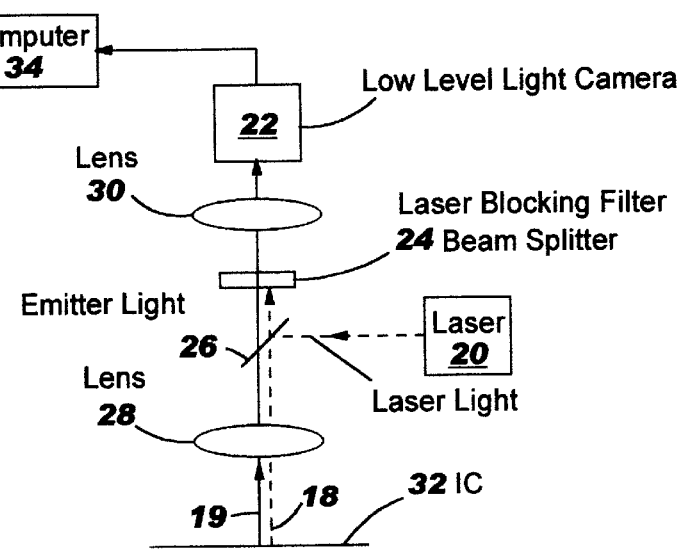
FIG. 2 illustrates an exemplary embodiment of a test apparatus used for monitoring polysilicon gate defects pursuant to the present invention.

A defect 17 is present in the test structure, shown at the bottom of the middle gate area 14 in FIG. 1B, which is being tested for in the test apparatus shown in FIG. 2. The test apparatus directs a laser beam onto the diffusion pad 12, and then examines the test structure, particularly the polysilicon gate areas 14, for the presence of radiation (photons) 19 emitted by defects 17 therein.

The test structure comprises a diffusion pad 12 functioning as a photodiode specifically printed on the silicon chip to be used as a circuit stimulus by an incident laser beam, test structure designed to detect defects 17 which emit radiation in the visible and near infrared portions of the spectrum when functioning as a current path or as a secondary effect thereof, and circuit pathways 16 connecting the photodiode diffusion pad 12 to the test structure terminals.

During testing, an incident laser beam stimulates the diffusion pad photodiode region 12 to generate photo-voltages and photo-current across the test structure. The laser power is selected to provide adequate voltage to the test structure and adequate current to a defect 17 to cause it to emit light. During such testing, only defects in the test structure such as shorts in the silicon gates areas to the substrate or to the S/D diffusion 13, are likely to emit radiation in the visible and near infrared portions of the spectrum. The defects provide mechanisms similar to those in an LED (Light Emitting Diode) to generate and emit such radiation in the visible and near infrared portions of the spectrum.

FIG. 2 illustrates an exemplary embodiment of a test apparatus used for monitoring polysilicon gate defects, which includes a laser probe having one or more lasers 20, an extremely low light level camera 22, an optical filter 24 blocking radiation at the laser wavelength, optics 26, 28 and 30 to join and focus the laser beam onto the IC test structure 32 and return an image of the IC test structure chip 32, and a computer 34 having a frame acquisition capability.

In operation, the optics 26 and 28 focus the laser beam 18 onto the photodiode region 12. A photo-voltage is thus created across the test structure.

The laser power is selected to provide adequate voltage to the test structure and adequate current to a defect 17 to cause it to emit light. An ArIon (blue) laser provides a suitable power laser beam and wavelength. The emitted, light is captured by the optics 28 and focused through the optical filter 24 and optics 30 onto the low light level camera 22. The optical filter 24 is selected to block any radiation at the laser wavelength.

The digital image captured by the camera 22 is then processed by the computer 34 to detect the presence and relative locations of any defects in the test structure. In one embodiment, the laser 20 power can be controlled by the computer 34 to acquire multiple test condition images for comparison.

While several embodiments and variations of the present invention for a method and structure for monitoring polysilicon gate defects are described in detail herein, it should be apparent that the disclosure and teachings of the present invention will suggest many alternative designs to those skilled in the art.

Having thus described our invention, what we claim as new, and desire to secure by Letters Patent is:

1. A method of detecting a gate defect in a silicon chip comprising a polysilicon gated field effect transistor in a semiconductor device wherein said defect causes the generating and emitting of radiation in the visible and near infrared portions of the spectrum responsive to stimulation by incident light, comprising the steps of:

a. providing the semiconductor device with a photodiode electron-generating region comprises a diffused region of the silicon chip to be used as a circuit stimulus in response to said incident light;

b. illuminating the photodiode region of the semiconductor device with incident light at a first wavelength to stimulate the photodiode region of said semiconductor device;

c. detecting light emitted from polysilicon gate areas of the silicon chip at a second wavelength at a further location of said semiconductor device responsive to the detection of a defect in said silicon chip at said location remote from the illuminated region, providing the silicon chip with conductive paths connecting the photodiode electron-generating region to terminals of the polysilicon gate areas; and d. filtering light emitted at the second wavelength by the defect at said location of the semiconductor device to eliminate therefrom light emitted at the first wavelength.

2. A method of detecting defects in a semiconductor device as claimed in claim 1, further comprising illuminating the photodiode region with a laser beam.

3. A method of detecting defects in a semiconductor device as claimed in claim 2, wherein the power of the laser beam is varied to provide multiple images under different test conditions.

4. A method of detecting defects in a semiconductor device as claimed in claim 1, further including forming an image of light emitted by the semiconductor device.

5. A method of detecting defects in a semiconductor device as claimed in claim 4, further including capturing and analyzing the image in a computer having a frame acquisition capability.

* * * * *